United States Patent
Zolotukhin et al.

(10) Patent No.: US 6,967,018 B2
(45) Date of Patent: Nov. 22, 2005

(54) ADIPONECTIN GENE THERAPY

(75) Inventors: Sergei Zolotukhin, Gainesville, FL (US); Michael D. Tennant, Seattle, WA (US)

(73) Assignee: Applied Genetic Technologies Corporation, Alachua, FL (US)

( * ) Notice: Subject to any disclaimer, the term of this patent is extended or adjusted under 35 U.S.C. 154(b) by 210 days.

(21) Appl. No.: 10/341,972

(22) Filed: Jan. 13, 2003

(65) Prior Publication Data

US 2003/0147855 A1    Aug. 7, 2003

Related U.S. Application Data

(60) Provisional application No. 60/347,411, filed on Jan. 11, 2002.

(51) Int. Cl.$^7$ .................... A01N 63/00; A61K 48/00
(52) U.S. Cl. ................. 424/93.2; 435/455; 435/456
(58) Field of Search .................. 424/93.2; 514/44; 435/455, 456

(56) References Cited

U.S. PATENT DOCUMENTS 5,858,351 A * 1/1999 Podsakoff et al. ......... 424/93.2
2003/0100500 A1 * 5/2003 Fruebis et al. ................. 514/12

FOREIGN PATENT DOCUMENTS

WO    WO 01/32868 A1    5/2001

OTHER PUBLICATIONS

Anderson et al., Nature, vol. 392, pp. 25-30, 1998.*
Verma, Nature, vol. 389, pp. 239-242, 1997.*
Kmiec, American Scientist, 1999, 87, 240-247.*
Juengst, BMJ, 2003, 326: 1410-11.*
Orkin et al., Dec. 7, 1995, "Report and Recommendation of the Panel to Assess the NIH investment in Research and Gene Therapy", issued by the National Institute of Health.*
Monahan et al., Molecular Medicine Today, 2000, 4: 433-440.*
Okamoto et al., "Adiponectin Reduces Atherosclerosis in Apolipoprotein E-Deficient Mice," Circulation, 22: 2767, 2002.
Scherer et al., "A novel Serum Protein Similar to Clq, Produced Exclusively in Adipocytes," The Journal of Biological Chemistry, 270: 26746-26749, 1995.
Hu et al., "AdipoQ Is a Novel Adipose-specific Gene Dysregulated in Obesity," The Journal of Biological Chemistry, 271: 10697-10703, 1996.
Maeda et al., "cDNA Cloning and Expression of a Novel Adipose Specific Collagen-like Factor, apM1 (Adipose Most Abundant Gene Transcript 1)," Biological and Biophysical Research Communications, 221: 286-289, 1996.
Nakano et al., "Isolation and Characterization of GBP28, a Novel Gelatin-Binding Protein Purified from Human Plasma," J. Biochem, 120: 803-812, 1996.
Arita et al., "Paradoxical Decrease of an Adipose-Specific Protein, Adiponectin, in Obesity," Biochemical and Biophysical Research Communication, 257: 79-83, 1999.
Fruebis et al., "Proteolytic cleavage product of 30-kDA adipocyte Complement-related protein increases fatty acid oxidation in muscle and causes weight loss in mice," PNAS, 98: 2005-2010, 2001.
Yamauchi et al., "The fat-derived hormone adiponectin reverses insulin resistance associated with both lipoatrophy and obesity," Nature Medicine, 7: 941-946, 2001.

* cited by examiner

Primary Examiner—Joseph Woitach
Assistant Examiner—Brian Whiteman
(74) Attorney, Agent, or Firm—Edwards & Angell, LLP

(57) ABSTRACT

Adiponectin cDNA was cloned into AAV serotypes 1, 2, and 5-based expression vectors. Virions containing these vectors were administered to the livers of rat subjects via portal vein injection. A single injection of $6 \times 10^{11}$ virions of the vector caused a sustained and statistically significant reduction in body weight of the treated animals compared to the control animals. This occurred in the absence of side effects. Compared to control animals, the subject rats also exhibited reduced adipose tissue mass, reduced appetite, improved insulin sensitivity, and improved glucose tolerance.

18 Claims, 7 Drawing Sheets

ADIPONECTIN GENE THERAPY

CROSS REFERENCE TO RELATED APPLICATION

The present application claims the priority of U.S. provisional application No. 60/347,411 filed Jan. 11, 2002.

STATEMENT AS TO FEDERALLY SPONSORED RESEARCH

The invention was made with U.S. government support under grant number DK58193 awarded by the National Institutes of Health. The U.S. government may have certain rights in the invention.

FIELD OF THE INVENTION

The invention relates generally to fields of biology, endocrinology, gene therapy. More particularly, the invention relates to a method of modulating adiponectin activity in a subject using a recombinant adeno-associated virus (rAAV) vector.

BACKGROUND

Although the occurrence of obesity and the development of type 2 diabetes mellitus are tightly intertwined, the biological mechanisms underlying this relationship are incompletely understood. The symptoms of diabetes-insulin resistance, relative insulin hyposecretion, and hyperglycemia-have been hypothesized by some to be caused by obesity. Others, however, had suggested just the opposite-that obesity is caused by the symptoms of diabetes. For example, a recent study suggested that insulin resistance might contribute to the development of obesity. Fruhbeck et al., Am J Physiol Endocrinol Metab, 280:E827–47, 2001.

Insight into the relationship between diabetes and obesity has been gained through research into adipose tissue physiology. Recent studies have shown that, in addition to storing triglycerides, adipose tissue functions as an active endocrine organ capable of secreting a variety of factors that affect whole-body energy homeostasis. These factors, collectively termed "adipocytokines" or "adipokines" (Matsuzawa et al., Ann NY Acad Sci, 892:146–54, 1999) include: leptin, tumor necrosis factor (TNF)-α (Hotamisligil, G S, J Intern Med, 245:621–5, 1999), plasminogen-activator inhibitor type 1 (PAI-1) (Shimomura et al., Nat Med, 2:800–3, 1996), adipsin (White et al., J Biol Chem, 267:9210–3, 1992), resistin (Steppan et al., Nature, 409:307–12, 2001) and adiponectin.

Adiponectin, also known as AdipoQ, apM1, GBP28 or Acrp30 (Scherer et al., J Biol Chem, 270:26746–9, 1995; Hu et al., J Biol Chem, 271:10697–703, 1996; Maeda et al., Biochem Biophys Res Commun, 221:286–9, 1996; and Nakano et al., J Biochem (Tokyo), 120:803–12, 1996), is a polypeptide consisting of an N-terminal collagenous domain and a C-terminal globular domain. Serum levels of adiponectin are significantly decreased in both obesity and type 2 diabetes, indicating a possible metabolic role or relationship to insulin resistance. Scherer et al., J Biol Chem, 270:26746–9, 1995; Arita et al., Biochem Biophys Res Commun, 257:79–83, 1999. Consistent with this, a recent report by Fruebis et al. (Proc Natl Acad Sci USA, 98:2005–10, 2001) implicated a proteolytic fragment of adiponectin as an acute stimulator of fatty-acid oxidation by muscle. Other recent reports showed a possible causal role of adiponectin in the development of insulin resistance. Fruebis et al., Proc Natl Acad Sci USA, 98:2005–10, 2001; Yamauchi et al., Nat Med, 7:941–6, 2001.

While the research into adipose tissue physiology has not yet rendered a clear and complete explanation of the mechanisms underlying the relationship between diabetes and obesity, it has provided several new avenues to explore for developing new treatments for these disorders. In fact, many prospective treatments involving modulation of adipokine levels have been attempted with mixed results.

SUMMARY

The invention relates to methods and compositions for modulating adiponectin nucleic acid and/or protein levels in a subject. In the experiments described below, adiponectin cDNA was cloned into AAV serotypes 1, 2, and 5-based expression vectors (i.e., rAAV-Acrp30). Virions containing these vectors were administered to the livers of rat subjects via portal vein injection. A single injection of $6 \times 10^{11}$ virions of the vector caused a sustained and statistically significant reduction in body weight of the treated animals compared to the control animals. This occurred in the absence of side effects. Compared to control animals, the subject rats also exhibited reduced adipose tissue mass, reduced appetite, improved insulin sensitivity, and improved glucose tolerance.

Accordingly, the invention features a nucleic acid including a first AAV terminal repeat (TR); a second AAV TR; and interposed between the first and second AAV TRs, a nucleotide sequence that encodes at least a portion of an adiponectin protein that has at least one functional activity of native adiponectin. The nucleotide sequence can be one derived from a mammal such as a mouse, rat, or human. It can also be one that encodes a full-length adiponectin protein or a fragment thereof (e.g., the active globular domain of adiponectin). The TRs can be derived from a number of different serotypes. For example, one of the TRs can be derived from AAV serotypes 1, 2, or 5.

In variations of the invention, the nucleotide sequence can further include an expression control sequence. The expression control sequence can be one that effects tissue-specific (e.g., liver-specific or muscle specific) expression of the nucleotide sequence. It can be, for example, a chicken β-actin promoter or a cytomegalovirus enhancer operably linked to the nucleotide sequence. The nucleic acid can be included within a cell and/or included within an AAV virion.

In another aspect, the invention features a method of modulating adiponectin protein levels in a subject. This method includes the step of administering a nucleic acid of the invention into the subject. In variations of the methods of the invention, the modulation of adiponectin protein levels results in a reduction of weight gain, an increase in insulin sensitivity, an increase in glucose tolerance, and/or a reduction of appetite in the subject. In the method of the invention, the nucleic acid can be administered to the subject by intravenous or intramuscular injection.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes VII, Oxford University Press: New York, 1999. Commonly understood definitions of virology terms can be found in Granoff and Webster, Encyclopedia of Virology, 2nd edition, Academic Press: San Diego, Calif., 1999; and Tidona and Darai, The Springer Index of Viruses, 1st edition, Springer-Verlag: New York, 2002. Commonly understood definitions of microbiology can be found in Singleton and Sainsbury, Dictionary of Microbiology and Molecular Biology, 3rd edition, John Wiley & Sons: New York, 2002.

As used herein, phrase "nucleic acid" means a chain of two or more nucleotides such as RNA (ribonucleic acid) and DNA (deoxyribonucleic acid). The phrases "adiponectin gene," "adiponectin nucleic acid," as used herein mean a nucleic acid that encodes a adiponectin protein. Examples of adiponectin nucleic acids include a native adiponectin-encoding nucleic acid sequence, e.g., the native human (Genbank Accession No. AF304467), rat (Genbank Accession No. NM 144744), and mouse (Genbank Accession Nos. AF304466, NM 009605) genes; a native form adiponectin cDNA; a nucleic acid having sequences from which an adiponectin cDNA can be transcribed; and/or allelic variants and homologs of the foregoing.

As used herein, "protein" or "polypeptide" mean any peptide-linked chain of amino acids, regardless of length or post-translational modification, e.g., glycosylation or phosphorylation. By the phrase "adiponectin protein" is meant an expression product of an adiponectin nucleic acid from any species, such as a native adiponectin protein, or a protein that shares at least 65% (but preferably 75, 80, 85, 90, 95, 96, 97, 98, or 99%) amino acid sequence identity with one of the foregoing and displays a functional activity of a native adiponectin protein. A "functional activity" of a protein is any activity associated with the physiological function of the protein. For example, functional activities of a native adiponectin protein may include the ability to reduce body weight gain and insulin resistance when administered to a subject.

When referring to a nucleic acid molecule or polypeptide, the term "native" refers to a naturally-occurring (e.g., a "wild-type" [WT]) nucleic acid or polypeptide. A "homolog" of an adiponectin gene from one species of organism is a gene sequence encoding an adiponectin polypeptide isolated from an organism of a different species. Similarly, a "homolog" of a native adiponectin polypeptide is an expression product of an adiponectin gene homolog.

The phrase "expression control sequence" refers to any genetic element (e.g., polynucleotide sequence) that can exert a regulatory effect on the replication or expression (transcription or translation) of another genetic element. Common expression control sequences include promoters, polyadenylation signals, transcription termination sequences, upstream regulatory domains, origins of replication, internal ribosome entry sites (IRES), enhancers, and the like. A "tissue specific expression control sequence" is one that exerts a regulatory effect on the replication or expression (transcription or translation) of another genetic element in only one type of tissue or a small subset of tissues.

A first nucleic acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

As used herein, the term "vector" refers to a nucleic acid molecule capable of transporting another nucleic acid to which it has been linked, e.g., a plasmid. One type of preferred vector is an episome, i.e., a nucleic acid capable of extra-chromosomal replication. Preferred vectors are those capable of autonomous replication and/or expression of nucleic acids to which they are linked. An "rAAV vector" is a vector that include nucleic acid sequences derived from AAV.

By use of "virion" is meant a completed virus particle that contains a nucleic acid and a protein coat (capsid). An "rAAV virion" is a virion that includes nucleic acid sequences and/or proteins derived from AAV.

As used herein, the terms "terminal repeat" or "TR" mean a nucleic acid sequence derived from an AAV that is required in cis for replication and packaging of AAV.

Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control. The particular embodiments discussed below are illustrative only and not intended to be limiting.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1:
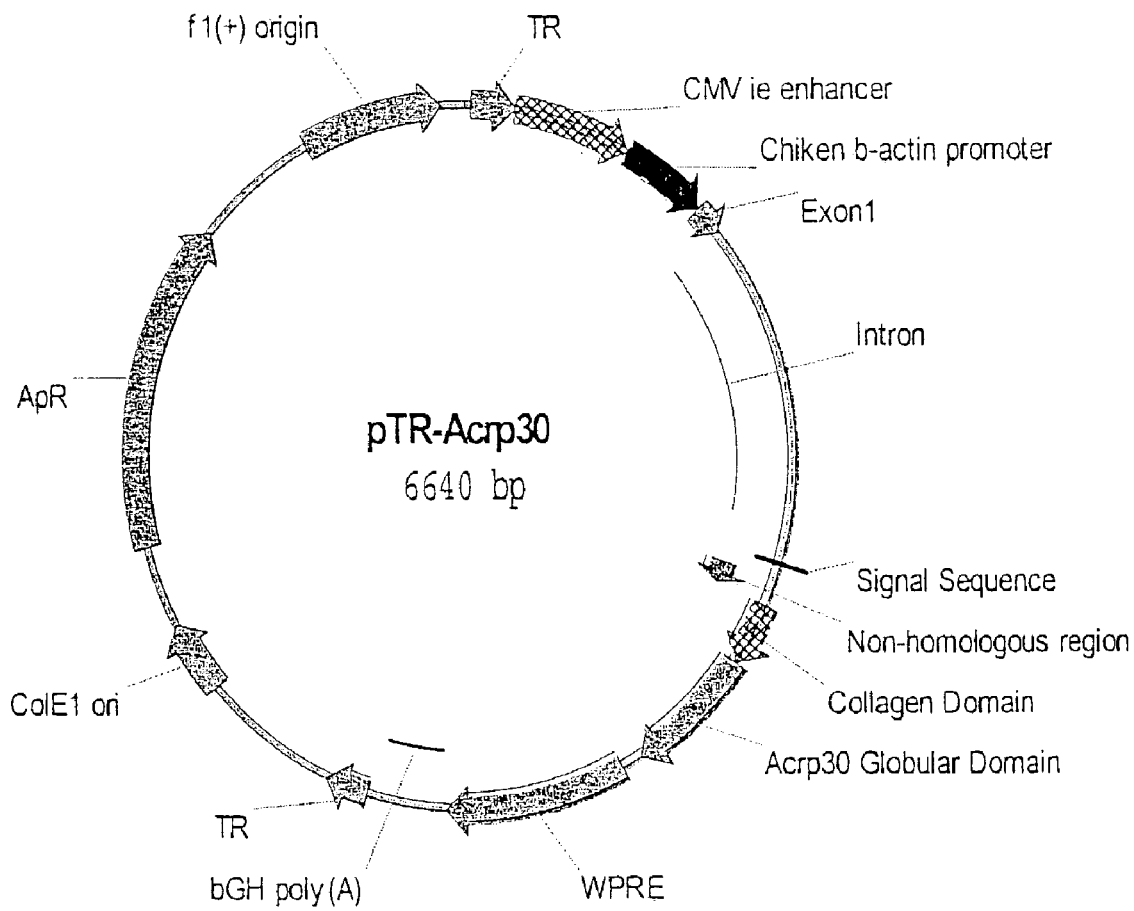
FIG. 1 is a schematic illustration of rAAV vector plasmid pTR-Acrp30.

The invention provides methods and compositions for modulating adiponectin protein and nucleic acid levels in a subject. In the experiments described below, adiponectin nucleic acids and proteins were delivered to rats using a rAAV vector. Compared to control rats, the subject rats exhibited reduced adipose tissue mass, reduced appetite, improved insulin sensitivity, and improved glucose tolerance.

The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1–3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859–1862, 1981, and Matteucci et al., J. Am. Chem. Soc., 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy are described in, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

AAV Vectors

The invention utilizes rAAV vectors and virions for delivering an adiponectin-encoding nucleic acid to a subject. AAV is an attractive vector system for human gene therapy because it is non-pathogenic for humans, it has a high frequency of integration, and it can infect nondividing cells, thus making it useful for delivery of genes into mammalian cells both in tissue culture and in whole animals. Muzyczka, Curr. Top. Microbiol. Immunol., 158:97–129, 1992.

AAV is a helper-dependent parvovirus in that it requires coinfection with another virus (either adenovirus [Ad] or a member of the herpes virus family) to undergo a productive infection in cultured cells. Muzyczka, N., Curr. Top. Microbiol. Immunol., 158:97–129, 1992. In the absence of coinfection with helper virus, AAV establishes a latent state by insertion of its genome into human chromosome 19, where it resides in a latent state as a provirus. Kotin et al., Proc. Natl. Acad. Sci. USA, 87:2211–2215, 1990; Samulski et al., EMBO J. 10:3941–3950, 1991. When a cell carrying an AAV provirus is superinfected with a helper virus, the AAV genome undergoes rescue and proceeds through a normal productive infection. Samulski et al., Cell, 33:135–143, 1983; McLaughlin et al., J. Virol., 62:1963–1973, 1988; Kotin et al., Proc. Natl. Acad. Sci. USA, 87:2211–2215, 1990; Muzyczka, N., Curr. Top. Microbiol. Immunol., 158: 97–129, 1992.

Recent studies have demonstrated AAV to be a potentially useful vector for gene delivery. LaFace et al., Viology., 162:483–486, 1998; Zhou et al., Exp. Hematol. (NY), 21:928–933, 1993; Flotte et al., PNAS 90:10613–10617, 1993; and Walsh et al., Blood 84:1492–1500, 1994. Recombinant AAV vectors have been used successfully for in vitro and in vivo transduction of marker genes (Kaplitt et al., Nature Genetics, 8:148–154, 1994; Lebkowski et al., Mol. Cell. Biol. 8:3988–3996, 1988; Samulski et al., J. Virol., 63:3822–3828, 1989; Shelling, A. N., and Smith, M. G., Gene Therapy, 1:165–169, 1994; Yoder et al., Blood, 82: suppl. 1:347A, 1994; Zhou et al., J. Exp. Med., 179:1867–1875, 1994; Hermonat, P. L. and Muzyczka, N., Proc. Nalt. Acad. Sci. USA., 81:6466–6470, 1984; Tratschin et al., Mol. Cell. Biol., 4:2072–2081, 1984; McLaughlin et al., J. Virol., 62:1963–1973, 1988) as well as genes involved in human diseases (Flotte et al., Am. J. Respir. Cell Mol. Biol., 7:349–356, 1992; Luo et al., Blood, 82:suppl. 1,303A, 1994; Ohi et al., Gene, 89L:27914 282, 1990; Walsh et al., PNAS 89:7257–7261, 1992; Wei et al., Gene Therapy, 1:261–268, 1994). Recently, an AAV vector has been approved for phase I human trials for the treatment of cystic fibrosis.

Typically, rAAV virus (virions) is made by cotransfecting a plasmid containing the gene of interest flanked by the two AAV TRs (McLaughlin et al., J. Virol., 62:1963–1973, 1988; Samulski et al., J. Virol., 63:3822–3828, 1989) and an expression vector containing the WT AAV coding sequences without the TRs, for example pIM45. McCarty et al., J. Virol., 65:2936–2945, 1991. The cells are also infected or transfected with Ad or plasmids carrying the Ad genes required for AAV helper function. rAAV virus (virion) stocks made in this fashion are contaminated with Ad which must be physically separated from the rAAV particles (for example, by cesium chloride density centrifugation). Alternatively, Ad vectors containing the AAV coding regions or cell lines containing the AAV coding regions and some or all of the Ad helper genes could be used. Yang et al., J. Virol., 68:4847–4856, 1994; Clark et al., Human Gene Therapy, 6:1329–1341, 1995. Cell lines carrying the rAAV DNA as an integrated provirus can also be used (Flotte et al., Gene Therapy, 2:29–37, 1995) in the production of infectious virions.

An rAAV vector of the invention is a recombinant AAV-derived nucleic acid sequence that includes at least those AAV sequences required in cis for replication and packaging (e.g., functional TRs) of the virus. In some applications, rAAV vectors contain a non-AAV nucleic acid. Non-AAV nucleic acids include, for example, marker or reporter genes (e.g., a nucleic acid encoding green fluorescent protein).

Non-AAV nucleic acids also include, for example, therapeutic genes (e.g., an adiponectin gene). Examples of useful rAAV vectors are those that have one or more AAV WT genes deleted in whole or in part, but retain functional flanking ITR sequences. Other useful rAAV vectors include those that contain rep and cap genes. rAAV vectors can be derived from any AAV serotype, including 1, 2, 3, 4, 5, 6, and 7.

AAV Serotypes 1, 2 and 5

The rAAV vectors and virions of the invention may be derived from any of several AAV serotypes. To develop optimized vectors for the delivery of therapeutic genes including adiponectin, rAAV vectors derived from AAV serotypes other than type 2 have been constructed. A new generation of rAAV vectors, based on different serotypes, with altered biodistribution and level of transgene product, has emerged as an alternative and more efficacious platform for gene delivery. Serotype-based AAV vectors have been shown to mediate transgene expression up to several logs higher compared to AAV-2. Halbert et al., J Virol, 75:6615–24, 2001; Chao et al., Mol Ther, 2:619–23, 2000; Duan et al., J Virol, 75:7662–71 2001; Zabner et al., J Virol, 74:3852–8, 2000. Research suggests that rAAV-1 vectors exhibit higher transgene expression in muscle compared to rAAV-2 vectors, and that rAAV-5 vectors exhibit higher transgene expression in hepatocytes (liver) compared to rAAV-2 vectors.

Because the site of action of adiponectin has yet to be determined (although early research suggests that adiponectin may act in either the liver or muscle), an adiponectin expression cassette has been packaged into three different capsid serotypes: 1, 2 and 5. This set of vectors may be tailored to a particular route of administration for the most efficacious expression of adiponectin in target tissues, namely liver and muscle. Accordingly, the increased transduction capabilities of AAV vectors 1 and 5 may be exploited to achieve higher expression of adiponectin in muscle and liver, respectively. Techniques involving nucleic acids and capsids of different AAV serotypes are known in the art and are described in Halbert et al., J. Virol., 74:1524–1532, 2000; Halbert et al., J. Virol., 75:6615–6624, 2001; and Auricchio et al., Hum. Molec. Genet., 10:3075–3081, 2001.

Pseudotyped Vectors

Another aspect of the invention relates to the administration of pseudotyped rAAV-Acrp30 vectors to a subject for controlling weight gain, glucose tolerance and insulin sensitivity, as well as appetite. Pseudotyped rAAV virions contain an rAAV vector derived from a particular serotype that is encapsidated within a capsid containing proteins of another serotype. Vectors of the invention include AAV2 vectors pseudotyped with a capsid gene derived from an AAV serotype other than 2 (e.g., AAV1, AAV3, AAV4, AAV5, AAV6 or AAV7 capsids). For example, particularly preferred vectors of the invention are AAV2 vectors encoding Acrp30 pseudotyped with a capsid gene derived from AAV serotypes 1 or 5. Techniques involving the construction and use of pseudotyped rAAV virions are known in the art and are described in Duan et al., J. Virol., 75:7662–7671, 2001; Halbert et al., J. Virol., 74:1524–1532, 2000; and Zolotukhin et al., Methods, 28:158–167, 2002.

rAAV Mutants

The invention provides methods for modulating adiponectin protein levels (e.g., for regulating weight gain, insulin sensitivity and glucose tolerance) by administering rAAV-Acrp30 vector-containing virions that have mutations within the virion capsid. For example, suitable rAAV mutants may have ligand insertion mutations for the facilitation of targeting AAV to specific cell types (e.g., hepatocytes). The construction and characterization of AAV capsid mutants including insertion mutants, alanine screening mutants, and epitope tag mutants is described in Wu et al., J. Virol., 74:8635–45, 2000. Pseudotyped rAAV virions that have mutations within the capsid may also be produced and purified according to methods of the invention. Techniques involving nucleic acids and viruses of different AAV serotypes are known in the art and are described in Halbert et al., J. Virol., 74:1524–1532, 2000; and Auricchio et al., Hum. Molec. Genet., 10:3075–3081, 2001. Other rAAV virions that can be used in methods of the invention include those capsid hybrids that are generated by molecular breeding of viruses as well as by exon shuffling. See Soong et al., Nat. Genet., 25:436–439, 2000; and Kolman and Stemmer Nat. Biotechnol., 19:423–428, 2001.

Nucleic Acids

The invention provides nucleic acids (polynucleotides) that include (1) a first AAV TR, (2) a second AAV TR, and interposed between the first and second AAV TRs, (3) a nucleotide sequence that encodes at least a portion of an adiponectin protein that has at least one functional activity of a native adiponectin ("adiponectin-encoding nucleotide sequence").

The AAV TR sequences that are contained within the nucleic acid can be derived from any AAV serotype (e.g., 1, 2, 3, 4, 5, 6 and 7) or can be derived from more than one serotype. For use in a vector, the first and second TRs should include at least the minimum portions of a WT or engineered TR that are necessary for packaging and replication.

The adiponectin-encoding nucleotide sequence can take many different forms. For example, the sequence may be a native mammalian adiponectin nucleotide sequence such as the mouse or human adiponectin nucleotide sequences deposited with Genbank as accession nos. AF304466/NM009605 and AF304467, respectively. Other native mammalian adiponectin nucleotide sequences that may be used within the invention include rat (accession nos. NM_144744, AY033885), canine (accession no. AF417206), and rhesus macaque (accession no. AF404407) nucleotide sequences.

The adiponectin-encoding nucleotide sequence may also be a non-native coding sequence which, as a result of the redundancy or degeneracy of the genetic code, encodes the same polypeptide as does a native mammalian adiponectin nucleotide sequence. Other adiponectin-encoding nucleotide sequences within the invention are those that encode fragments, analogs and derivatives of a native adiponectin protein. Such variants may be, e.g., a naturally occurring allelic variant of a native adiponectin-encoding nucleic acid, a homolog of a native adiponectin-encoding nucleic acid, or a non-naturally occurring variant of native adiponectin-encoding nucleic acid. These variants have a nucleotide sequence that differs from native adiponectin-encoding nucleic acid in one or more bases. For example, the nucleotide sequence of such variants can feature a deletion, addition, or substitution of one or more nucleotides of a native adiponectin encoding nucleic acid. Nucleic acid insertions are preferably of about 1 to 10 contiguous nucleotides, and deletions are preferably of about 1 to 30 contiguous nucleotides.

In some applications, variant adiponectin-encoding nucleotide sequences encode polypeptides that substantially maintain an adiponectin protein functional activity. For other applications, such variants encode polypeptides that lack or feature a significant reduction in an adiponectin protein functional activity. Where it is desired to retain a functional activity of native adiponectin protein, preferred variant nucleotide sequences feature silent or conservative nucleotide changes.

In other applications, variant adiponectin polypeptides displaying substantial changes in one or more functional activities of native adiponectin protein can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histadine, for (or by) an electronegative residue, e.g., glutamine or aspartine; or (d) a residue having a bulky side chain, e.g., phenylalanine, for (or by) one not having a side chain, e.g., glycine.

Naturally occurring allelic variants of a native adiponectin-encoding nucleic acid within the invention are nucleotide sequences isolated from a mammalian subject (e.g., human, mouse, rat, dog, and macaque) that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with a native adiponectin-encoding nucleic acid, and encode polypeptides having as at least one functional activity in common with a native adiponectin protein. Homologs of a native adiponectin-encoding nucleic acid within the invention are nucleotide sequences isolated from other species that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with a native adiponectin-encoding nucleic acid, and encode polypeptides having at least one functional activity in common with a native adiponectin protein.

Non-naturally occurring adiponectin-encoding nucleic acid variants are nucleotide sequences that do not occur in nature (e.g., are made by the hand of man), have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with a native adiponectin-encoding nucleic acid, and encode polypeptides having at least one functional activity in common with a native adiponectin protein. Examples of non-naturally occurring adiponectin nucleotide sequences are those that encode a fragment of an adiponectin protein, those that hybridize to a native adiponectin-encoding nucleic acid or a complement of a native adiponectin-encoding nucleic acid under stringent conditions, those that share at least 65% sequence identity with a native adiponectin-encoding nucleic acid or a complement of a native adiponectin-encoding nucleic acid, and those that encode an adiponectin fusion protein.

Nucleotide sequences encoding fragments of adiponectin protein are those that encode, e.g., 2, 5, 10, 25, 50, 100, 150, 200, or more amino acid residues of an adiponectin protein. A particularly useful fragment or portion of an adiponectin protein is the active globular domain of adiponectin (e.g., amino acids 110–247 or 104–247 of murine adiponectin). See Philipp et al., J. Biol. Chem. 270:26746–26749, 1995; and Fruebis et al., PNAS 98:2005–2010, 2001. The adiponectin-encoding nucleotide sequence can also be one that encodes an adiponectin fusion protein. Such a sequence can be made by ligating a first polynucleotide encoding an adiponectin protein fused in frame with a second polynucleotide encoding another protein (e.g., one that encodes a detectable label).

Expression Control Sequences

In addition to the AAV TRs and the adiponectin-encoding nucleotide sequence, the nucleic acids of the invention can also include one or more expression control sequences operatively linked to the adiponectin-encoding nucleotide sequence. Numerous such sequences are known. Those to be included in the nucleic acids of the invention can be selected based on their known function in other applications. Examples of expression control sequences include promoters, insulators, silencers, enhancers, initiation sites, termination signals, and polyA tails.

To achieve appropriate levels of adiponectin proteins, any of a number of promoters suitable for use in the selected host cell may be employed. For example, constitutive promoters of different strengths can be used to express adiponectin proteins.

Expression vectors and plasmids in accordance with the present invention may include one or more constitutive promoters, such as viral promoters or promoters from mammalian genes that are generally active in promoting transcription. Examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and CMV promoters. Examples of constitutive mammalian promoters include various housekeeping gene promoters, as exemplified by the β-actin promoter.

Inducible promoters and/or regulatory elements may also be contemplated for use with the nucleic acids of the invention. Examples of suitable inducible promoters include promoters from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline. The sterol regulatory-binding protein (SREBP-1c) promoter is another inducible promoter useful within the invention (Deng et al., Biochem. Biphys. Res. Commun 290:256–262, 2002; Kim et al., J. Clin. Invest. 101:1–9, 1998; and Azzout-Marniche et al., Biochem. J. 350 Pt 2:389–393, 2000). Expression of the SREBP-1c gene is induced by nutritional stimuli, in particular by insulin and glucose.

A rAAV vector has been constructed that encodes mouse Acrp30 under the control of a rat SREPB-1c promoter. The presence of this vector in a mammalian subject is expected to up-regulate the expression of adiponectin by hyperinsulinemia induced by overnutrition (a condition known to be associated with low serum adiponectin levels).

Tissue-specific promoters and/or regulatory elements are useful in certain embodiments of the invention. Examples of such promoters that may be used with the expression vectors of the invention include promoters from the transphyretin, α1-antitrypsin, plasminogen activator inhibitor type 1 (PAI-1), apolipoprotein AI and LDL receptor genes, specific for liver cells; and the utrophin promoter A and human dystrophin muscle specific promoters, specific for muscle cells.

The promoter used to express the adiponectin gene is not critical to the present invention. In the examples given, the human chicken β-actin promoter has been used (Miyazaki et al., Gene, 79:269–77, 1989) which results in the sustained, high-level expression of the foreign gene. However, the use of other promoters (such as viral, mammalian or cellular promoters) which are well known in the art, is also suitable to achieve expression of the adiponectin gene. Preferably the promoter will direct expression of an adiponectin-encoding nucleic acid in an amount sufficient to reduce body weight gain and appetite as well as increase insulin sensitivity in a subject.

Modulating Adiponectin Protein Levels in a Subject

The invention provides compositions and methods for modulating adiponectin protein levels in a subject using an rAAV vector. The method includes the step of administering to the subject a nucleic acid containing a first AAV TR, a second AAV TR, and a nucleotide sequence that encodes at least a portion of an adiponectin protein that has at least one functional activity of native adiponectin ("an AAV-adiponectin vector"). The subject can be animal into which a nucleic acid of the invention can be administered. In general, animals that typically express adiponectin such as mammals (e.g., human beings, dogs, cats, pigs, sheep, mice, rats, rabbits, cattle, goats, etc.) are suitable subjects.

Administration of rAAV-Acrp30 Compositions

Any suitable method for administering a nucleic acid to a subject may be used to administer an AAV-adiponectin nucleic acid, vector, or virion to the subject. For example, an nucleic acid, vector, or virion can be administered to a subject by parenteral administration (e.g., intravenous and/ or intramuscular injection). An AAV-adiponectin nucleic acid, vector, or virion can be delivered to a particular site by known methods. For example, to deliver an AAV-adiponectin nucleic acid, vector, or virion to the liver (a preferred target), intravenous injection of the portal vein may be performed. Intracranial injection or injection into peripheral (non-CNS) sites may also be used in certain applications. The effectiveness of particular protocols can be assessed using conventional clinical assays, e.g., examining the subject's visceral fat pad, its ability to normalize circulating glucose levels, and measuring the sensitivity of the subject's hepatocytes to insulin.

The nucleic acids, vectors, and virions of the present invention can be administered to a subject by ex vivo delivery, where cells not contained within a subject (e.g., cells isolated from a mammalian subject such as hepatocytes) are transduced with AAV-adiponectin nucleic acid or vector or infected with a rAAV-adiponectin virion in vitro, and the cells are then introduced into the subject (e.g., transduced isolated cells are delivered to the liver). In one example of a suitable ex vivo protocol, liver cells (e.g., hepatocytes) may be harvested from the subject and transduced with AAV-adiponectin nucleic acid or vector or infected with a rAAV-adiponectin virion in vitro. These genetically modified cells may then be transplanted back into the subject. Modified liver cells may be reintroduced into the subject's liver by any suitable delivery route (e.g., intravenous delivery to the portal vein). Microencapsulation of cells transduced with AAV-adiponectin nucleic acid or vector or infected with a rAAV-adiponectin virion in vitro modified ex vivo is another technique that may be used within the invention. Delivery of an adiponectin-encoding nucleic acid may also involve methods of ex vivo gene transfer using stem cells and progenitor cells. Such methods involve the isolation and expansion of selected stem or progenitor cells, introduction of a therapeutic gene into the cells ex vivo, and return of the genetically modified cells to the host. Autologous and allogeneic cell transplantation may be used according to the invention.

Parenteral administration of vectors or virions by injection can be performed, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the vectors or virions may be in powder form (e.g., lyophilized) for constitution with a suitable vehicle, for example, sterile pyrogen-free water, before use.

To facilitate delivery of the vectors or virions to a subject, the vectors or virions of the invention can be mixed with a carrier or excipient. Suitable carriers and diluents can be selected on the basis of mode and route of administration and standard pharmaceutical practice. Carriers and excipients that might be used include saline (especially sterilized, pyrogen-free saline) saline buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly preferred for delivery of vectors or virions to human subjects. A description of exemplary pharmaceutically acceptable carriers and diluents, pharmaceutical formulations, and methods for making such formulations can be found in, for example, *Remington's Pharmaceutical Sciences* (Remington: The Science and Practice of Pharmacy, 19th ed., A. R. Gennaro (ed), Mack Publishing Co., N.J., 1995).

Effective Doses

An effective amount is an amount which is capable of producing a desirable result in a treated subject (e.g., reduction of body weight gain, reduction of appetite, and increase of insulin sensitivity). As is well known in the medical and veterinary arts, dosage for any one mammal depends on many factors, including the subject's size, body surface area, age, the particular composition to be administered, time and route of administration, general health, and other drugs being administered concurrently. It is expected that a composition of rAAV-Acrp30 may be administered intravenously in the portal vasculature or intramuscularly in a dosage range of about $1\times10$ to $1\times10^{13}$ viral particles. Although these doses are based on experiments with small mammals, one of skill in the art, without undue experimentation, could determine appropriate doses for use in human subjects by employing known principles of pharmacology. Dosage treatment may be a single dose schedule or a multiple dose schedule.

EXAMPLES

The present invention is further illustrated by the following specific examples. The examples are provided for illustration only and are not to be construed as limiting the scope or content of the invention in any way.

The rAAV-Acrp30 system has been successfully tested in a rat model. The results of the studies described herein demonstrate the efficacy of rAAV vectors expressing adiponectin in obese animals in the absence of unwanted side effects. Several experimental and hypothetical studies in support of the invention are outlined below:

Example 1

Materials and Methods

Construction of pTR-Acrp30. cDNA coding for mouse adiponectin was obtained by reverse transcriptase PCR (RT-PCR)-mediated cloning using total RNA isolated from white adipose tissue (WAT). Upon sequence verification, the adiponectin cDNA was subcloned into an AAV2 transfer vector derived from pTR-UF2 (Zolotukhin et al., J Virol, 70:4646–54, 1996). The resulting plasmid, pTR-Acrp30 (FIG. 1) was subsequently used to package the adiponectin cassette.

FIG. 1 depicts pTR-Acrp30. The sequences featured on the plasmid map of pTR-Acrp30 are as follows: TR is the AAV2 terminal repeat sequence; CBA promoter includes the CMV intermediate early enhancer sequence, the chicken β-actin promoter, non-coding sequence (Exon 1) and intron from rabbit β-globin gene; the full-length mouse Acrp30 gene includes sequences coding for an endogenous signal peptide, non-homologous sequence, collagen domain peptide and active globular domain; WPRE is the woodchuck hepatitis virus post-transcription regulatory sequence; bGH poly(A) is the bovine growth hormone polyadenylation sequence.

Plasmid pTR-Acrp30 contains two AAV2 TR sequences (TR2). The mouse adiponectin cDNA (Acrp30) is driven by a chicken β-actin (CBA) promoter (Miyazaki et al., Gene 79:269–277, 1989) linked to a CMV enhancer. The WPRE posttranscriptional regulatory element is placed downstream to enhance the expression of the transgene (Donello et al., J. Virol. 72:5085–5092, 1998; and Loeb et al., Hum. Gene Ther. 10:2295–2305, 1999). Transcription of the transgene is terminated by the bovine growth hormone polyadenylation signal (pA).

Vertebrate animals. For DIO studies, Sprague-Dawley (SD) rats were purchased from Charles River Laboratories (Wilmington, Mass.). A large amount of information is available regarding the mechanisms of diet induced obesity in SD rats (Kakuma et al., Proc Natl Acad Sci USA, 97:8536–41, 2000). Weight gain regulation experiments that will be conducted are designed on the basis of this knowledge and thus, will be conducted in rats.

For portal vein injections animals were sedated by xylazine, 8 mg/kg, sc and 5 minutes later, 90 mg/kg ketamine, i.p. State of anesthesia was assessed by application of forceps to foot pad or tail. A ventral midline abdominal incision was made into the peritoneal cavity and the portal vein was exposed. AAV virions were administered into the portal vein using a 30 G needle cemented to a capillary pipette and driven by air pressure via rubber tubing and a Drummond self-locking double layer 0.8 µm filter. Hemostasis was achieved with application of a small piece of Gel-Foam directly on to the portal vein. Surgeries were performed on a thermo-regulated operating board designed to maintain a temperature of 37° C. Surgeries routinely took 10 min to perform.

Example 2

Modulation of Body Weight by Cytokine Vectors and Changes in Hypothalamic Gene Expression in rAAV-treated Rats A conceptual approach for a systemic, targeted alteration of metabolic pathways leading to a sustained loss of WAT in normal SD rats was undertaken. This study involved a central (intracerebroventricular, icv) administration of rAAV encoding either a lipostatic hormone, leptin, or anorexigenic cytokines of the IL6 family (CNTF and LIF). The respective ligands encoded by leptin, CNTF or LIF transgenes induced similar but not identical physiological responses as assessed by the reduction in body weight gain and changes in food intake. Sustained ectopic expression of rAAV-mediated transgenes resulted in either mild (CNTF) or severe (leptin and LIF) anorexia. This anorexia was not associated with long-term significant changes in caloric intake in the cases of CNTF and LIF.

Two distinct phases in response to transgenes were documented: 1) onset of phenotypic changes of body weight loss concomitant with statistically significant reduction in food intake (short-term, approximately 1 week); and 2) sustained maintenance of the lean phenotype that is not associated with long-term significant changes in caloric intake in the case of CNTF or LIF. The changes in gene expression pattern in the hypothalamus related to energy metabolism were further investigated using DNA microarray chip technology.

The effects of rAAV-administered cytokines upon gene expression in the hypothalamus were also analyzed. Changes in gene expression in the hypothalamus related to energy metabolism were investigated and the results yielded several genes that were either upregulated or downregulated by these cytokines.

For the experiment described herein, the ProbeProfiler™ was utilized. The results of two hierarchical clustering runs are provided, performed by GeneSpring software, using two sets of data derived from the same experiment. A dendrogram of clustered genes was obtained with the Affymetrix algorithm, while the GeneProfiler™ performed global normalization of the clustered genes. Due to the increased sensitivity of the latter approach, many more genes displaying statistically significant changes were detected. In addition, the clustering algorithm of the normalized database grouped LIF and CNTF gene expression patterns separate from GFP control and leptin groups, yet close together reflecting their functional similarity and relationship. Clustering of the normalized database provides more meaningful and abundant information, by more accurately reflecting the true biological meaning of the experiment.

Leptin, CNTF, and LIF induced a number of identical genes: 64 for the short-term experiment, 60 for the long-term. In general, the transgenes induced a wide array of changes in the expression of growth and trophic factors concomitant with profound alterations in downstream signal transduction pathways controlling cell differentiation and proliferation. Sustained expression of leptin, CNTF or LIF dramatically altered the expression of a wide variety of neuropeptides, neurotransmitters, their receptors and ion channels, which apparently resulted in both short- and long-term synaptic modifications, changes in neuronal transmission patterns and synaptic plasticity.

Microarray hybridization data for a subset of selected genes, showing differential expression, were validated and confirmed by Northern blot analysis, as well as by real-time RT-PCR analysis. Both independent assays were in general agreement with the microarray data for the selected genes.

An analysis of the gene profiling data is summarized as follows. Constitutive expression of pro-inflammatory cytokines LIF, CNTF, and leptin triggered the up-regulation of anti-inflammatory cytokine gene expression (IL-10, IL-13) and the down-regulation of pro-inflammatory cytokine gene expression (IL-6, IL-9, and endogenous LIF). The resulting neurological response resulted in anorexia (hypophagia) and was exacerbated by the acute induction of corticotrophin releasing hormone (CRH). Both CNTF and LIF, but not leptin, induced similar activation of the stress-response gene small heat shock protein (hsp27); and of the metallothionein (mt) gene. The immediate early transcript c-fos, induced by leptin (Gloaguen et al., Proc Natl Acad Sci USA, 94:6456–61, 1997; Hildinger et al., Molecular Therapy 3:S187, 2001), was much more strongly up-regulated by cytokine action, a fact that can be apparently explained by a higher abundance of CNTF and LIF receptors in the hypothalamus, as compared to Ob-Rb receptors. Similar induction was documented for the suppressor of cytokine signaling (SOCS-3), a putative leptin-resistance factor implicated in a negative feedback loop that restricts the activity of the cytokine class of ligands (Starr et al., Nature, 387:917–21,1997), of which leptin is a member.

Acute repression of neuropeptide Y (NPY) enhances sympathetic stimulation of brown adipose tissue (BAT) resulting in nearly complete depletion of WAT. Dramatic induction of CRH increased pituitary adrenocorticotrophic hormone (ACTH) release and subsequent secretion of glucocorticoids by the adrenal gland (HPA axis). Negative feedback regulation by high concentrations of stress-induced circulating glucocorticoids results in a long-term decline of hypothalamic CRH expression. The combination of chronically reduced NPY expression (orexigenic peptide) and increased cholecystokinin (CCK) expression (anorexigenic peptide) contributes to the maintenance of the lean phenotype during constitutive expression of leptin and LIF. The dramatic shift in the expression profile of neuropeptides correlates with increased levels of stress-related factors such as Hsp27, metallothionein and CREB-1. A shift in the balance of intracellular signals transmitted via JAK/STAT and MAPK pathways in favor of the former (i.e., SOCS-3 up-regulation) results in neogliogenesis as indicated by the up-regulation of the GFAP marker.

Although efficient when injected in the brain, these vector-encoded ligands were not nearly as successful upon peripheral administration, a more clinically relevant modality. In addition, leptin, as well as CNTF and LIF induced a cascade of changes in expression of hundreds of hypothalamic genes, many associated with stress and immune responses, signal transduction, neurotransmission and other crucial functions, as determined by DNA microarray analysis.

Example 3

Downregulation of Adiponectin Gene in Aging Rats cDNA for the mouse adipocyte hormone adiponectin was cloned using a PCR-mediated protocol. This cDNA was labeled with $^{32}P$ and was used as a probe in a Northern blot. Three distinct species of adiponectin-specific transcripts in rat adipocytes were detected. These mRNAs may encode the same or slightly different proteins. Adiponectin mRNA was reduced by greater than 40% in perirenal WAT (100±6.7 at 6 months vs. 59.4±4.5 at 30 months, p=0.001, N=6) and by 25% in retroperitoneal WAT (100±4.9 at 3 months vs. 76.1±3.8 at 24 months, p=0.0002, N=7) in the aged rat model.

Example 4

Adiponectin Activates AMPK via Threonine Phosphorylation

Data collected in several laboratories (reviewed in Winder et al., Am. J. Physiol. 277:E1–10, 1999) indicate that AMPK now appears to be a metabolic master switch, phosphorylating key target proteins that control flux through metabolic pathways of hepatic ketogenesis, cholesterol synthesis, and triglyceride synthesis. To test adiponectin signaling and activation of downstream pathways leading to phosphorylation of AMPK, an experiment using the murine cell line AML12 (Wu et al., PNAS 91:674–678, 1994) established from hepatocytes (ATCC #CRL-2254) was conducted. An exogenous ligand, murine adiponectin was purified according to Berg et al. (Nat. Med. 7:947–953, 2001) from 293 HEK (human embryonic kidney cells) cells transiently transfected with pTR-Acrp30.

AML12 cells were grown in D-MEM/F-12 media (GIBCO) supplemented with 10% fetal bovine serum (FBS) 40 ng/ml dexamethasone, and ITS (5 µg/ml insulin, 2.75 µg/ml trasferrin, 3.35 ng/ml Na-selenite). Before induction, cells were washed with phosphate buffered saline solution (PBS) and starved by incubation for 16 hrs in the same media supplemented with 40 ng/ml dexamethasone, 0.3% bovine serum albumin (BSA), and ITS. Induction was conducted by incubating cells with either $H_2O_2$ for 20 minutes (positive control), or with murine adiponectin at different concentrations for one hour. A Western blot analysis of dose-responsive phosphorylation of AMP-activated protein kinase induced by adiponectin in murine hepatocyte cell line AML12 was performed. Adiponectin activated downstream signaling via AMPK within the physiological range of its in vivo concentrations.

Example 5

Regulation of Body Weight by rAAV-Acrp30

Figure 2:
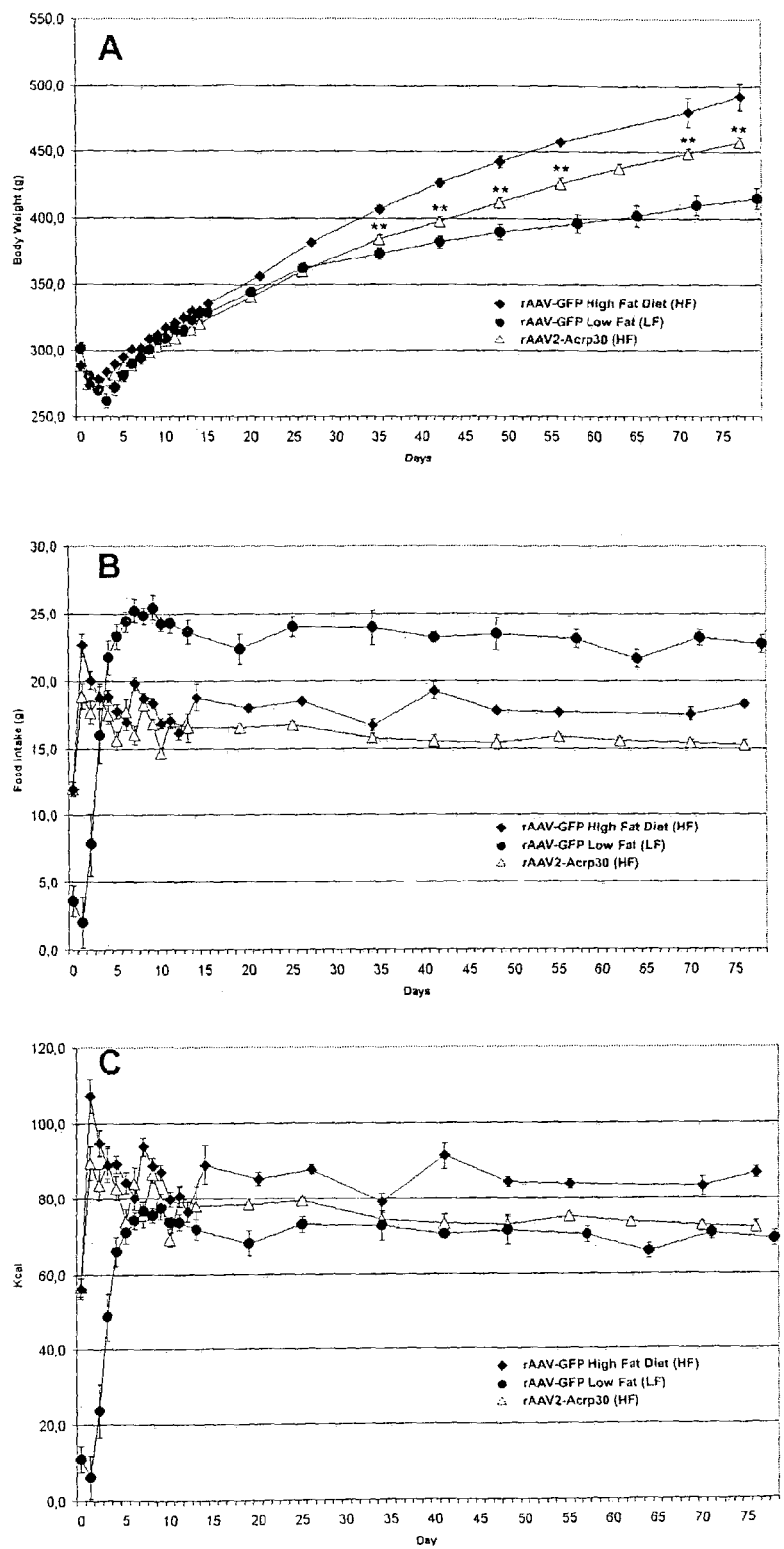
FIG. 2 is a series of graphs showing effects of peripherally administered (portal vein injection) rAAV2-Acrp30 in diet-induced obesity (DIO) male rats. A: change in body weight (BW). B: change in food intake (FI). C: change in ingested Kcal/day (FI, normalized for diet fat content, or metabolizable energy). Filled circles—rats injected with rAAV20GFP (n=4), fed a low fat (LF) diet (5% fat, negative control); filled diamonds—rats injected with rAAV2-GFP (n=4), fed a high fat (HF) diet (45% fat), DIO control; open triangles—rats injected with rAAV2-Acrp30 vector (n=5), fed a HF diet (45% fat). ** indicate P<0.01 by two-tail T-test as compared to rats fed a HF diet.

Adiponectin cDNA was cloned from mouse WAT and an AAV2-based vector expressing it was constructed (FIG. 1). The long-term expression of the vector was tested upon portal vein injection (targeting liver) of physical particles of this vector into DIO male rats. In one exemplary experiment, the treated group consisted of 5 animals and the control group consisted of 4 animals. From a single peripheral injection, a sustained and statistically significant reduction in body weight was observed. This experiment demonstrated that the administration of an rAAV vector encoding adiponectin to rats fed a high fat diet resulted in a restraint of body weight gain. The results showed, for the first time, that a single peripheral injection of $6 \times 10^{11}$ physical particles of this vector resulted in a sustained and statistically significant reduction in body weight (FIG. 2A). The body weight reduction was accompanied by a statistically significant reduction in food intake (FIG. 2B, 2C).

Example 6

Construction of rAAV Vectors

Figure 7:
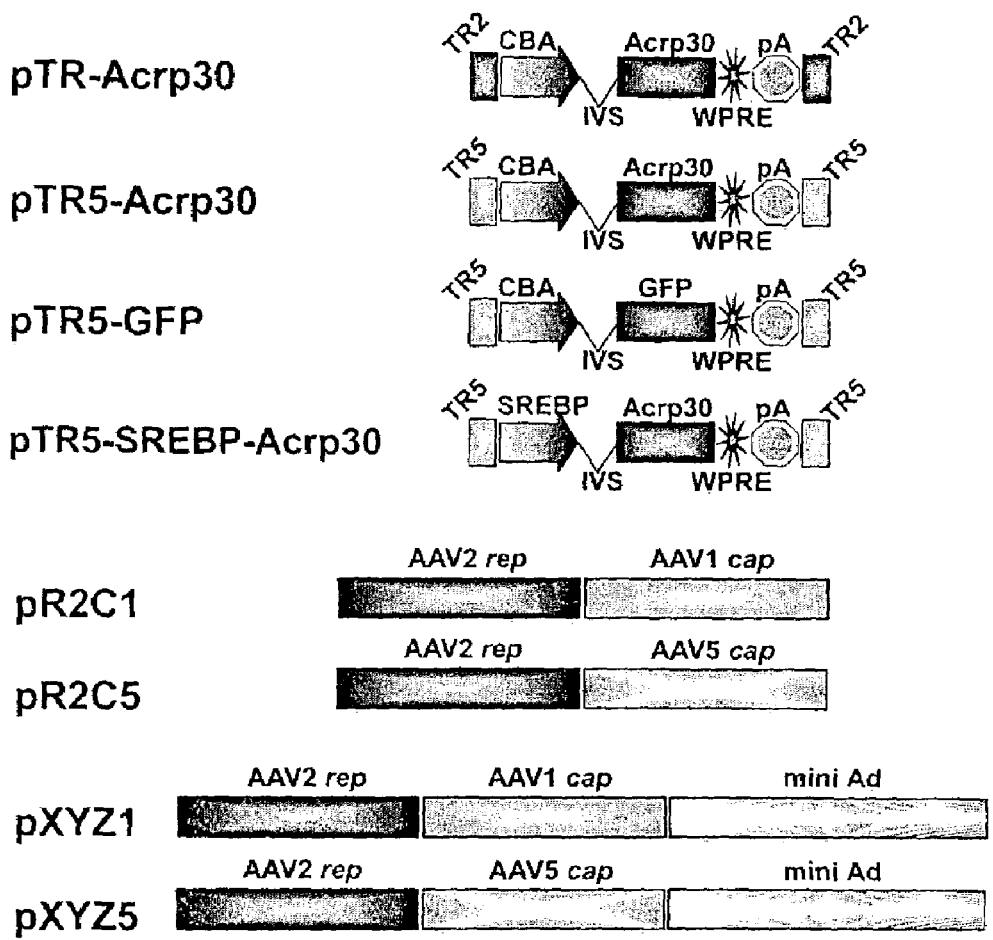
FIG. 7 is a diagram of AAV transfer vectors and helper plasmids.

A set of vectors and helper plasmids for types 1 and 5 has been constructed and tested. A diagram of AAV transfer vectors and helper plasmids is shown in FIG. 7. An AAV2/1 helper plasmid to pseudotype AAV2 DNA with an AAV1 capsid was constructed. For AAV5, both AAV2- and AAV5TRs-based vector plasmids were developed to compare side-by-side relative contribution of TRs and capsids to transduction efficiencies.

AAV helper plasmids were constructed by attaching the open reading frame (ORF) coding for Rep68/78 of AAV2 virus to the ORF coding for cap genes of other serotypes. pTR5-Acrp30 contains the same transgene cassette as pTR-Acrp30 subcloned into an AAV5 TR sequences (TR5) background. pTR5-GFP is identical to the latter AAV5 vector with "humanized" GFP cDNA substituted for adiponectin; in pTR5-SREBP-Acrp30 expression of adiponectin is driven by the rat SREBP promoter (Deng et al., Biochem. Biophys. Res. Commun. 290:256–262, 2002). pR2C1, a pACG2 derivative (Li et al., J. Virol., 71:5236–5243, 1997), is a hybrid helper plasmid containing an ORF coding for AAV2 rep genes from the plasmid linked to the ORF coding for AAV1 cap genes, which was amplified by a PCR-mediated protocol from wt AAV1 DNA. pR2C5 contains the AAV2 rep gene ORF linked to the ORF coding for AAV5 cap genes, and is derived from pAAV5-2 (Chiorini et al., J. Virol., 73:1309–1319, 1999). pXYZ1 and pXYZ5 contain rep2cap1 and rep2cap5 helper cassettes respectively, inserted into a pXYZ background. pXYZ, a mini Ad plasmid helper containing E2A, E4, and VA genes of Ad5, was constructed from pAdEasy (He et al., PNAS 95:2509–2514, 1998). Plasmids pXYZ1 and pXYZ5 were used to support pseudotyping of AAV2-TR-containing cassettes into AAV1 and AAV5 capsids without the need for an additional Ad helper plasmid.

Construction of transfer vectors. cDNA coding for mouse adiponectin was obtained by RT-PCR-mediated cloning using total RNA isolated from WAT. Upon sequence verification, the adiponectin cDNA was subcloned into an AAV2 transfer vector derived from pTR-UF2 (Zolotukhin et al., J Virol, 70:4646–54, 1996). The resulting plasmid, pTR-Acrp30 (FIG. 1), was subsequently used to package adiponectin cassette in AAV2 vector, as well as AAV1 and 5 pseudotyped vectors.

To package adiponectin into an AAV5 vector, the entire transgene cassette was subcloned into an AAV5 TR vector background (pTR5-Acrp30). The same backbone was used to design a control vector encoding the GFP reporter gene, which was substituted for Acrp30. In the current studies, "true" type AAV5 produced about 5-fold higher titers as compared to pseudotyped AAV5 vectors.

Purification of rAAV Virions. Protocols used to purify rAAV virion stocks are described in Zolotukhin et al., Methods 28:158–167, 2002. These protocols involve an iodixanol step gradient followed by either affinity Heparin (e.g., for purification of rAAV2) or ion-exchange chromatography (e.g., for purification of rAAV1 and rAAV5).

Example 7

Reduction of Body Weight and Food Intake by Administration of rAAV1-Acrp30 and rAAV5-Acrp30

Purified rAAV1-Acrp30 and rAAV5-Acrp30 virions were injected into the portal veins (rAAV5-Acrp30, $10^{12}$ particles/injection) of female SD rats. rAAV1-Acrp30 virions are pseudotyped virions that contain AAV1 capsid protein and an AAV2-based vector. rAAV5-Acrp30 virions are true-type virions containing AAV5 capsid protein and an AAV5-based vector. Two control cohorts were also injected with rAAV-GFP vectors (portal vein, $10^{12}$ particles/injection).

Figure 3:
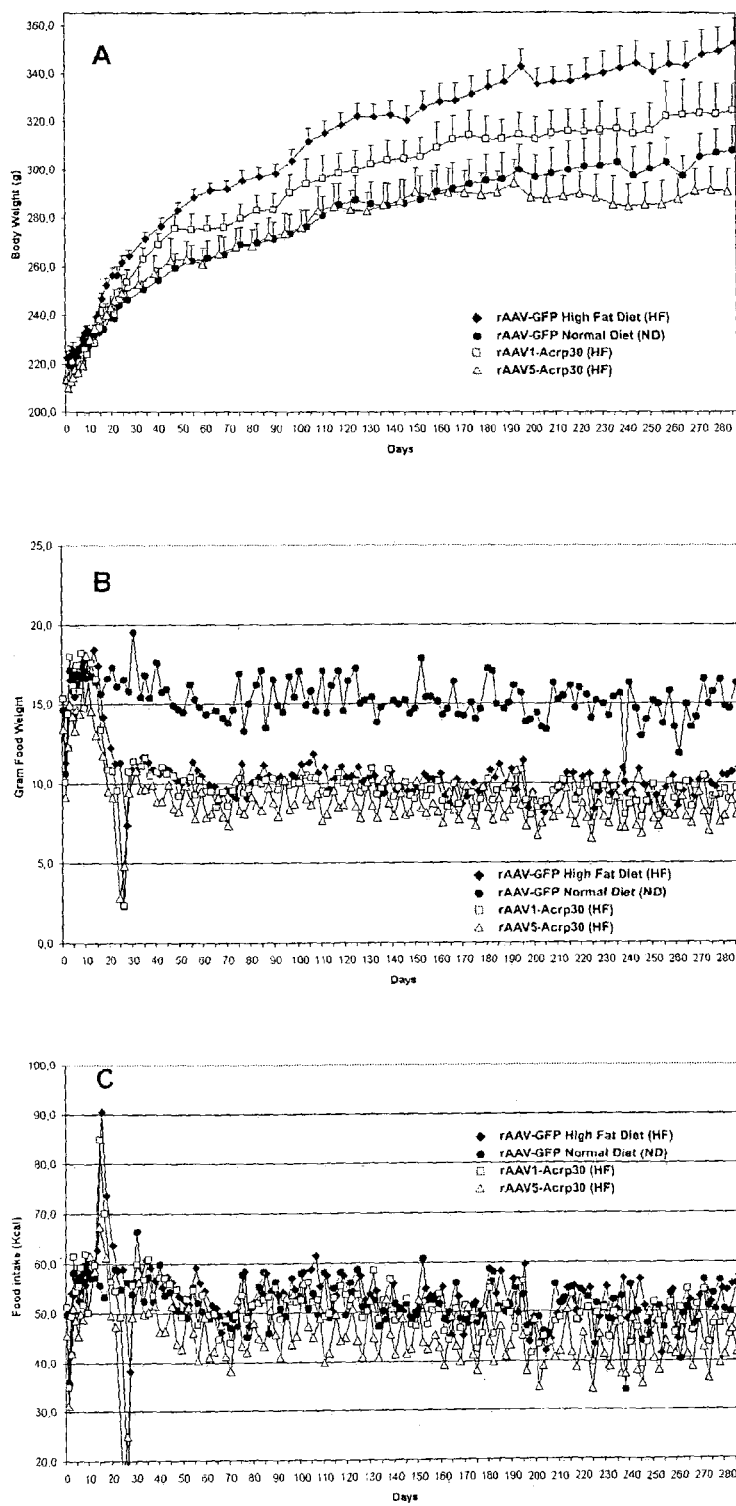
FIG. 3 is a series of graphs showing effects of peripherally administered rAAV1-Acrp30 and rAAV5-Acrp30 in DIO female rats. A: change in BW. B: change in FI. C: change in ingested Kcal/day (FI, normalized for diet fat content, or metabolizable energy). Filled circles—rats injected with rAAV2-GFP (n=6), fed a normal diet, (negative control); filled diamonds—rats injected with rAAV2-GFP (n=6), fed a HF diet (60% fat) diet, DIO control; open rectangles—rats injected with rAAV1-Acrp30 vector (n=6), fed a HF diet; open triangles—rats injected with rAAV5-Acrp30 vector (n=6), fed a HF diet.
Figure 4:
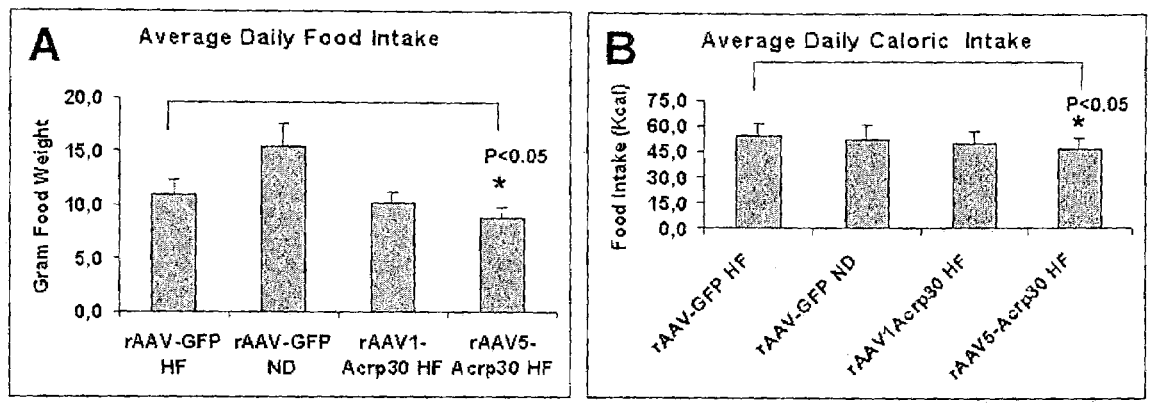
FIG. 4A is a graph showing average daily food intake in treated rats. HF—high fat diet (60%). ND—normal diet.
FIG. 4B is a graph showing average daily calorie intake in treated rats. HF—high fat diet (60%). ND—normal diet.

After animals regained pre-surgery FI parameters, three groups (treated with rAAV5-Acrp30, rAAV1-Acrp30, and rAAV-GFP) were switched to a high-calorie (60% fat) diet, while one control group (injected with rAAV-GFP) was maintained on a normal diet. Both groups of rats treated with rAAV-delivered adiponectin displayed a reduction of BW as compared to the control group fed a HF diet (FIG. 3A). rAAV5-Acrp30 appeared to be more efficacious than rAAV1-Acrp30, mediating complete ablation of the high calorie diet effect on BW gain. The FI data are consistent with the experiment obtained with rAAV-Acrp30 type 2 vectors: rats injected with rAAV-Acrp30 consumed on average less food (FIG. 3B, 3C). Numbers from the experiments shown in FIGS. 3B and 3C were averaged and are presented in the bar graphs of FIG. 4 (FIG. 4A, 4B). These graphs show that there was indeed a statistically significant reduction in daily food intake (hence calories) in animals injected with rAAV5-Acrp30. For rAAV1-Acrp30, there was also a downward trend, although not statistically significant (consistent with smaller changes in body weight in animals treated with rAAV1-Acrp30 as compared to animals treated with rAAV5-Acrp30).

Although preliminary, these results substantiate the hypothesis that peripheral treatment with rAAV-Acrp30 could modulate the energy metabolism of the whole body, creating in effect a compelling animal model to study the functions of a novel hormone adiponectin.

Example 8

Improvement of Glucose Tolerance by rAAV1-Acrp30 and rAAV5-Acrp30

Figure 5:
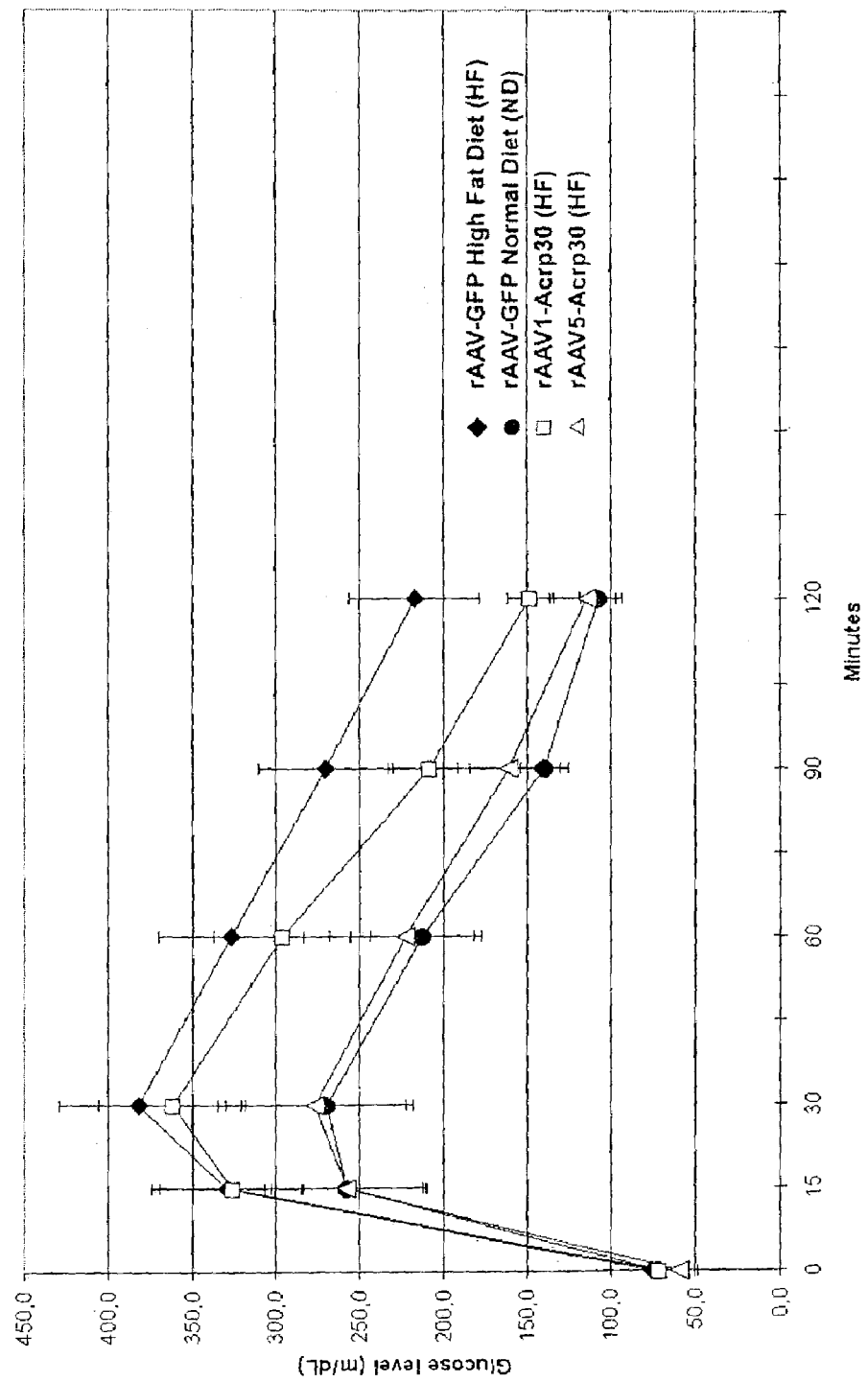
FIG. 5 is a graph showing an effect of peripherally administered rAAV1-Acrp30 and rAAV5-Acrp30 on glucose tolerance in DIO female rats. Filled circles—rats injected with rAAV2-GFP (n=6), fed a normal diet, (negative control); filled diamonds—rats injected with rAAV2-GFP (n=6), fed a HF diet (60% fat), DIO control; open rectangles—rats injected with rAAV1-Acrp30 vector (n=6), fed a HF diet; open triangles—rats injected with rAAV5-Acrp30 vector (n=6), fed a HF diet.
Figure 6:
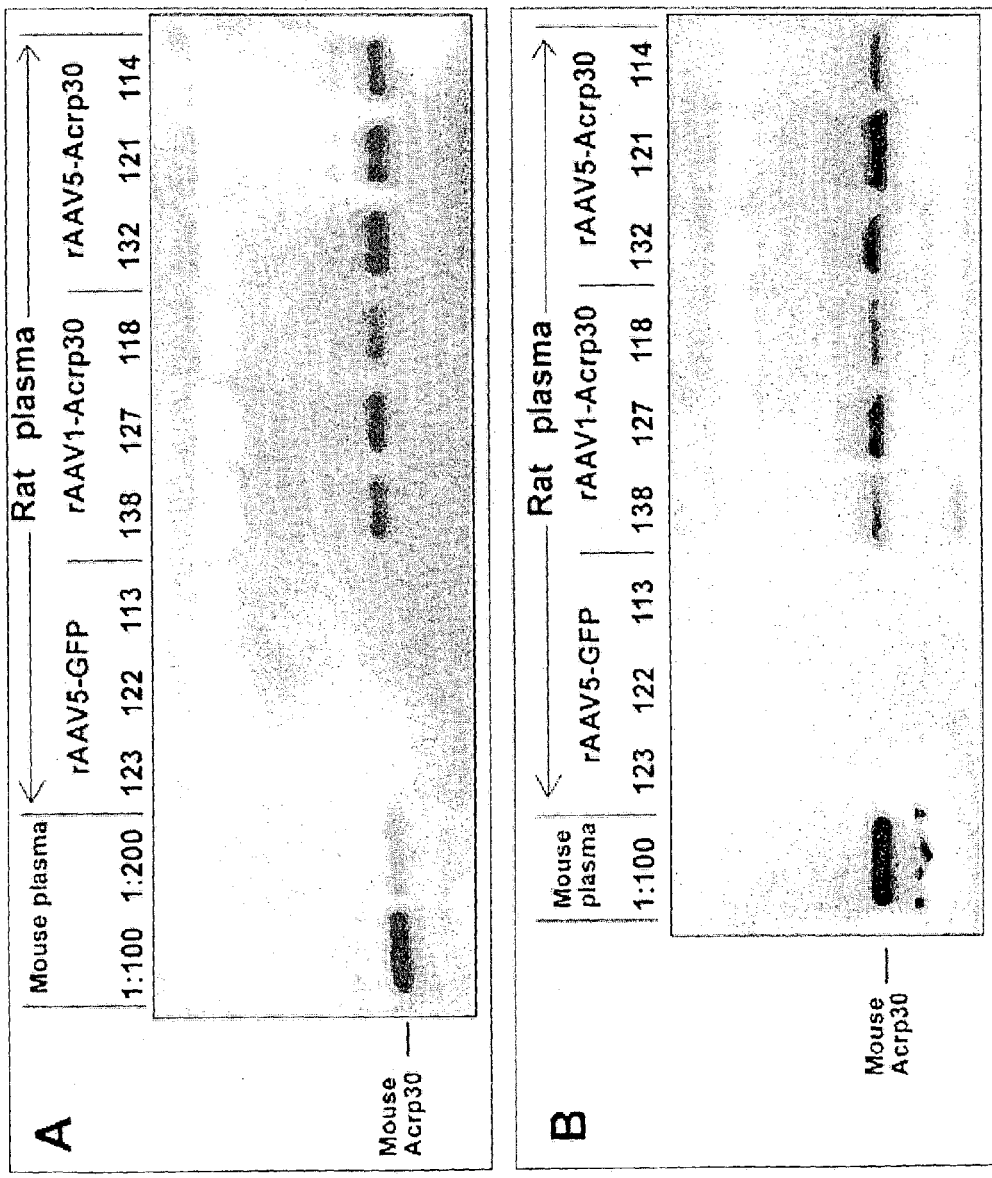
FIG. 6 is a Western blot analysis of proteins in plasma from rats injected with rAAV1-Acrp30 and rAAV5-Acrp30. A: plasma from rats at day 40 post-treatment. B: plasma from rats at sacrifice (day 297 post-treatment). Plasma from normal mouse was used as a positive control sample (diluted at 1:100, or 1:200). Numbers above each lane refer to individual experimental animals.

To determine the effect of sustained Acrp30 transgene expression on plasma glucose levels, an Intraperitoneal Glucose Tolerance Test (IP GTT) was performed on day 190 post injection. After overnight fast, unanaesthetized rats were injected with a 50% glucose solution (2 g/kg$^{-1}$ BW). Plasma glucose values were examined 0, 15, 30, 60, 90, and 120 min after glucose injection (FIG. 5).

Administration of rAAV5-Acrp30 resulted in improved insulin sensitivity and glucose tolerance, correction of hyperglycemia associated with obesity, and reduction of adipose tissue mass. All of the above mentioned effects were described in long-term experiments upon single injection of virions containing rAAV-Acrp vectors, serotypes 1, 2, or 5. Virions containing serotype 5 capsid protein appeared to be the most efficacious, consistent with earlier observations of higher transduction efficacies of AAV serotype 5 in liver (Mingozzi et al., J. Virol., 76:10497–10502, 2002).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing adiponectin protein levels in a mammal, comprising injecting a mammal in need thereof, a recombinant adeno-associated (rAAV) expression vector comprising a nucleic acid sequence that encodes full-length adiponectin polypeptide operably linked to an expression control sequence.

2. The method of claim 1 wherein the nucleic acid sequence encodes mouse adiponectin.

3. The method of claim 1 wherein the nucleic acid sequence encodes rat adiponectin.

4. The method of claim 1 wherein the nucleic acid sequence encodes human adiponectin.

5. The method of claim 1 wherein the expression vector control sequence effects expression of adinonectin polypeptide in the liver.

6. The method of claim 1 wherein the expression vector control sequence effects expression of adiponectin polypeptide in muscle.

7. The method of claim 1 wherein the expression control sequence is chicken β-actin promoter.

8. The method of claim 1 wherein the rAAV is serotype 1.

9. The method of claim 1 wherein the rAAV is serotype 5.

10. The method of claim 1 wherein the rAAV is serotype 2.

11. The method of claim 1 wherein the rAAV vector is comprised within an AAV virion.

12. The method of claim 1 wherein the increase in adiponectin polypeptide levels reduces weight gain in the mammal.

13. The method of claim 1 wherein the increase in adiponectin polypeptide levels increases insulin sensitivity in the mammal.

14. The method of claim 1 wherein the increase in adiponectin polypeptide levels increases glucose tolerance in the mammal.

15. The method of claim 1 wherein the increase in adiponectin polypeptide levels in the mammal.

16. The method of claim 1 wherein the injecting is by intravenous injection.

17. The method of claim 16 wherein the intravenous injection is into the portal vein.

18. The method of claim 1 wherein the injecting is intramuscular injection.

* * * * *